United States Patent
Zhang et al.

(10) Patent No.: US 11,638,700 B2
(45) Date of Patent: May 2, 2023

(54) IRON/SHIKONIN NANO-COMPOSITE AND USE THEREOF AND METHOD FOR PREPARING THE SAME BY SUPERMOLECULAR SELF-ASSEMBLY

(71) Applicant: Jilin University, Jilin (CN)

(72) Inventors: Hao Zhang, Jilin (CN); Wenjie Feng, Jilin (CN); Yi Liu, Jilin (CN); Lening Zhang, Jilin (CN); Wanrui Shi, Jilin (CN)

(73) Assignee: Jilin University, Changchun (CN)

( * ) Notice: Subject to any disclaimer, the term of this patent is extended or adjusted under 35 U.S.C. 154(b) by 60 days.

(21) Appl. No.: 17/335,565

(22) Filed: Jun. 1, 2021

(65) Prior Publication Data

US 2022/0071927 A1   Mar. 10, 2022

(30) Foreign Application Priority Data

Sep. 10, 2020 (CN) .......................... 202010945688.6

(51) Int. Cl.
*A61K 31/122* (2006.01)
*A61K 47/52* (2017.01)
*A61P 35/00* (2006.01)
*A61K 9/14* (2006.01)

(52) U.S. Cl.
CPC ............ *A61K 31/122* (2013.01); *A61K 9/143* (2013.01); *A61K 47/52* (2017.08); *A61P 35/00* (2018.01)

(58) Field of Classification Search
CPC .................................................. A61K 31/122
See application file for complete search history.

(56) References Cited

FOREIGN PATENT DOCUMENTS

| JP | S6289772 A | * | 4/1987 | ............. C09B 67/00 |
| JP | H06100569 A | * | 4/1994 | ................ C07F 1/08 |

* cited by examiner

*Primary Examiner* — Brian J Davis
(74) *Attorney, Agent, or Firm* — Faegre Drinker Biddle & Reath LLP (57) ABSTRACT

An iron/shikonin nano-composite and a use thereof, and a method for preparing the same by supermolecular self-assembly, belonging to the technical field of functional materials. The composite consists of shikonin and ferric ions, wherein shikonin is coordinated with the ferric ions, and the hydroxyl and carbonyl groups in shikonin are coordinated with the ferric irons to form a complex, which is then assembled by π-π stacking and hydrophobic interactions to form a nano-composite which exhibits glutathione response. The composite is obtained by the following steps: adding an aqueous solution of a ferric salt and an organic solvent solution of shikonin in sequence into water while stirring at ambient temperature, continuously stirring at ambient temperature, and centrifuging the resulting mixture to purify, thereby obtaining an iron/shikonin nano-composite in the resulting solution.

14 Claims, 12 Drawing Sheets

IRON/SHIKONIN NANO-COMPOSITE AND USE THEREOF AND METHOD FOR PREPARING THE SAME BY SUPERMOLECULAR SELF-ASSEMBLY

CROSS REFERENCE TO RELATED APPLICATION

This application claims the priority of Chinese Patent Application No. 202010945688.6, entitled "Iron/shikonin nano-composite and use thereof and method for preparing the same by supermolecular self-assembly" filed with the China National Intellectual Property Administration on Sep. 10, 2020, which is incorporated herein by reference in its entirety.

TECHNICAL FIELD

The present disclosure belongs to the technical field of functional materials, and particularly relates to an iron/shikonin nano-composite, a use thereof and a method for preparing the same by supermolecular self-assembly. The method makes it possible to effectively increase the solubility of shikonin in water, and in terms of the treatment of cancer, the nano-composite has great functions of chemical kinetic treatment and chemotherapy, and could be used for preparing drugs for treating cancer.

BACKGROUND

Shikonin is a major biologically active ingredient extracted from alkanet, and is a kind of polyphenolic compound. It has been widely concerned by people in terms of the treatment of cancer. Many studies have shown that shikonin can play an anti-cancer role by inhibiting the proliferation of cancer cells, inducing apoptosis, and inhibiting the migration and invasion of cancer cells; it can also activate anti-tumor immunity through various molecular mechanisms. However, shikonin has a poor solubility in water, a low bioavailability, and defects similar with those of many other small molecule drugs such as extensive metabolism at the initial stage, low accumulation amount within tumor cells and low selectivity to tumor cells, resulting in a certain limitation to its therapeutic effect. To address the above problems, researchers have loaded shikonin into nano-materials such as liposome nano-particles, to apply to cancer treatment. In addition to enhanced permeability and retention effect (EPR), nano-drugs have many advantages such as increased solubility of hydrophobic drugs. However, the loss and release of drugs in the process of transporting shikonin-loaded nano-materials to tumor areas need to be solved. Moreover, it is also a big challenge to design nano-materials so that drug release could be triggered at the lesion site. In addition, the therapeutic performance of these nano-drugs is not satisfactory, so that researchers are prompted to incorporate more therapeutic methods into nano-preparations to improve their anti-cancer effects. Therefore, it is necessary to design a nano-drug which exhibits an increased shikonin solubility in water, reduces the drug loss and could function sufficiently to achieve anticancer effect.

Nano-drugs designed and prepared by metal coordination exhibits effectively increased stability of nano-drug system, and especially nano-drugs prepared by synergistic assembly through π-π stacking and hydrophobic interactions exhibit improved stability and multiple responsiveness.

In recent years, the design of novel bioresponsive nano-materials has aroused great interest, among which nano-materials with glutathione response in tumor areas have received extensive attention. The concentration of glutathione within tumor cells is about 2-10 mM, while about 2-20 μM in extracellular environment, and the concentration of glutathione within tumor cells is many times higher than that within normal cells. Therefore, glutathione is considered as an ideal and common internal stimulus, and the response to glutathione could be used to quickly destroy the stability of intracellular nano-carriers, so as to realize the efficient release of intracellular drugs.

SUMMARY

One objective of the present disclosure is to provide an iron/shikonin nano-composite, so as to increase the solubility of shikonin in water, increase the bioavailability thereof, and meanwhile to improve the cancer treatment effect by stimulating response release and introducing various cancer treatment methods. Another objective of the present disclosure is to provide a method for preparing an iron/shikonin nano-composite by supermolecular self-assembly. Yet another objective of the present disclosure is to provide a use of the iron/shikonin nano-composite in preparing a drug for treating cancer.

To achieve the above objectives, the present disclosure provides the following technical solutions:

In a first aspect, the present disclosure provides an iron/shikonin nano-composite, consisting of shikonin and ferric ions, wherein shikonin is coordinated with the ferric ions, and the hydroxyl and carbonyl groups in shikonin are coordinated with the ferric irons to form a complex, which is then assembled by π-π stacking and hydrophobic interactions to form a nano-composite which exhibits glutathione response.

In some embodiments, the iron/shikonin nano-composite has a diameter of 10-200 nm, and a concentration of the iron/shikonin nano-composite in water is not lower than 100 mg/mL, which is much higher than the solubility of shikonin in water (shikonin is generally considered insoluble in water).

In a second aspect, the present disclosure provides a method for preparing an iron/shikonin nano-composite, comprising the following steps:

adding an aqueous solution of a ferric salt into water while stirring at ambient temperature, and then adding an organic solvent solution of shikonin;

continuously stirring at ambient temperature, and then centrifuging the resulting mixture to purify, to obtain an iron/shikonin nano-composite solution; and drying the iron/shikonin nano-composite solution to obtain an iron/shikonin nano-composite solid powder.

In some embodiments, the organic solvent is miscible with water and may be selected from the group consisting of methanol, ethanol, isopropanol, acetonitrile, glycerol, acetone, dimethyl sulfoxide, tetrahydrofuran and dimethylformamide; the ferric salt may be selected from the group consisting of ferric chloride, ferric nitrate and ferric sulfate; a molar ratio of the ferric salt to shikonin is in a range of (0.1-12):1; in the organic solvent solution of shikonin, a concentration of shikonin is in a range of 1-10 mg/mL; in the aqueous solution of the ferric salt, a concentration of the ferric salt is in a range of 50-800 mg/mL; continuous stirring at ambient temperature comprises maintaining stirring for 30 min to 24 h.

Compared with the prior art, the method according to the present disclosure has the following beneficial effects:

(1) The iron/shikonin nano-composite prepared in the present disclosure exhibits a good biocompatibility and biological stability.

(2) The iron/shikonin nano-composite prepared in the present disclosure makes it possible to significantly increase the solubility of shikonin in water and improve the bioavailability thereof, and shikonin functions as the skeleton in the nano-composite, which does not involve the loading and consumption of shikonin drugs.

(3) The iron/shikonin nano-composite prepared in the present disclosure exhibits a glutathione response, and may be disassembled in a tumor cell environment to release iron and shikonin. Iron and hydrogen peroxide within cells may undergo Fenton reaction to generate hydroxyl radicals, so as to realize chemical kinetic therapy; the released shikonin can play the role of chemotherapy. After further surface modification, the nano-composites could also be more effectively applied to the field of nano-drug, thereby being used for preparing drugs for treating cancer.

(4) The iron/shikonin nano-composite prepared in the present disclosure can be doped with other metal ions in the synthesis process to prepare the multi-metal/shikonin nano-composite.

(5) The method provided by the present disclosure is carried out under mild experimental conditions, which may be ambient temperature; it is simple to operate without any complex synthesis and preparation process; moreover, it make it possible to produce a product with a uniform and adjustable size, and has a good experimental repeatability, so that it make mass preparation possible, and is suitable for industrial production.

BRIEF DESCRIPTION OF THE DRAWINGS

FIG. 8A and FIG. 8B show the response test curve of the iron/shikonin nano-composite as prepared in Example 7 to a glutathione solution with a concentration of 2 mM.

DETAILED DESCRIPTION

The present disclosure will be further illustrated with examples below, but these examples are not intended to limit the present disclosure.

Example 1

Figure 1:
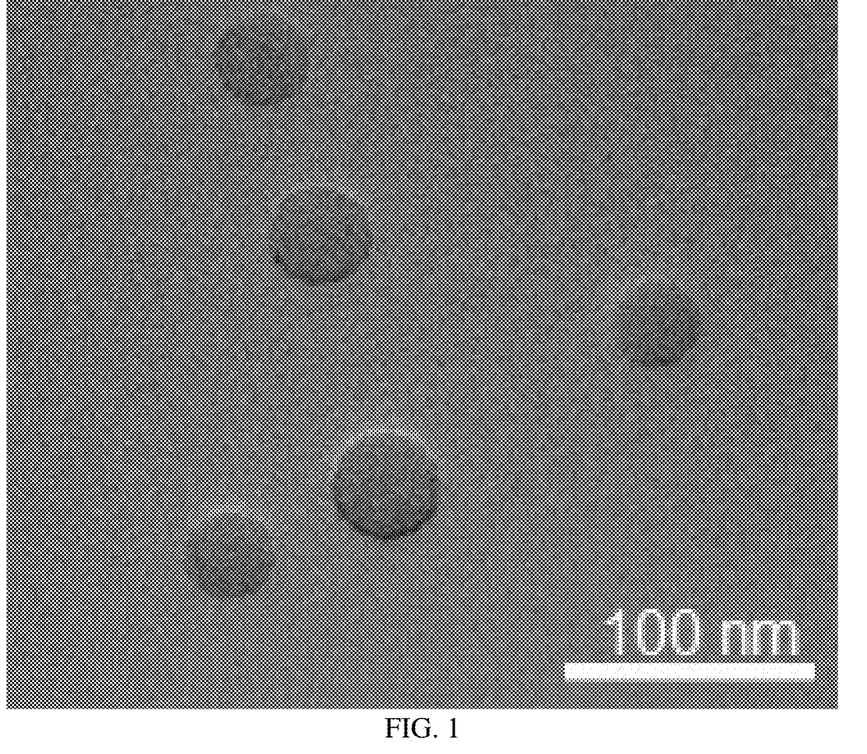
FIG. 1 shows a transmission electron microscope photograph of the iron/shikonin nano-composite as prepared in Example 1, with a size of 30 nm.

Ferric chloride hexahydrate was dissolved in water to obtain a ferric chloride aqueous solution with a concentration of 100 mg/mL; shikonin was dissolved in ethanol to obtain a shikonin ethanol solution with a concentration of 5 mg/mL. 1 mL of the ferric chloride aqueous solution and 5 mL of the shikonin ethanol solution were added in sequence into 40.75 mL of water while stirring at ambient temperature. After stirring at ambient temperature for 1 hour, the resulting mixture was centrifuged at a rotation speed of 15000 rpm for 15 min, for 3 times in total, to obtain an iron/shikonin nano-composite solution, in which the nano-composite has an average size of 30 nm; finally the iron/shikonin nano-composite was dissolved in water to obtain a nano-composite solution with a concentration of 100 mg/mL.

Example 2

Figure 2:
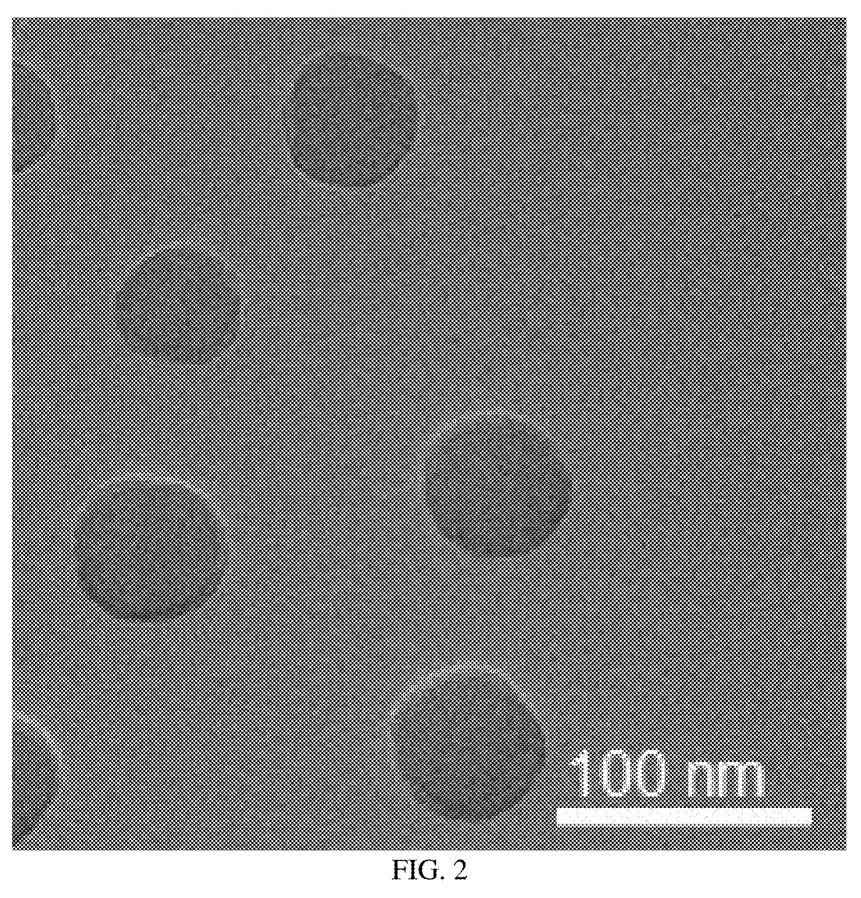
FIG. 2 shows a transmission electron microscope photograph of the iron/shikonin nano-composite as prepared in Example 2, with a size of 50 nm.

Ferric chloride hexahydrate was dissolved in water to obtain a ferric chloride aqueous solution with a concentration of 100 mg/mL; shikonin was dissolved in ethanol to obtain a shikonin ethanol solution with a concentration of 5 mg/mL. 500 μL of the ferric chloride aqueous solution and 5 mL of the shikonin ethanol solution were added in sequence into 41.25 mL of water while stirring at ambient temperature. After stirring at ambient temperature for 1 hour, the resulting mixture was centrifuged at a rotation speed of 15000 rpm for 15 min, for 3 times in total, to obtain an iron/shikonin nano-composite solution, in which the nano-composite has an average size of 50 nm.

Example 3

Figure 3:
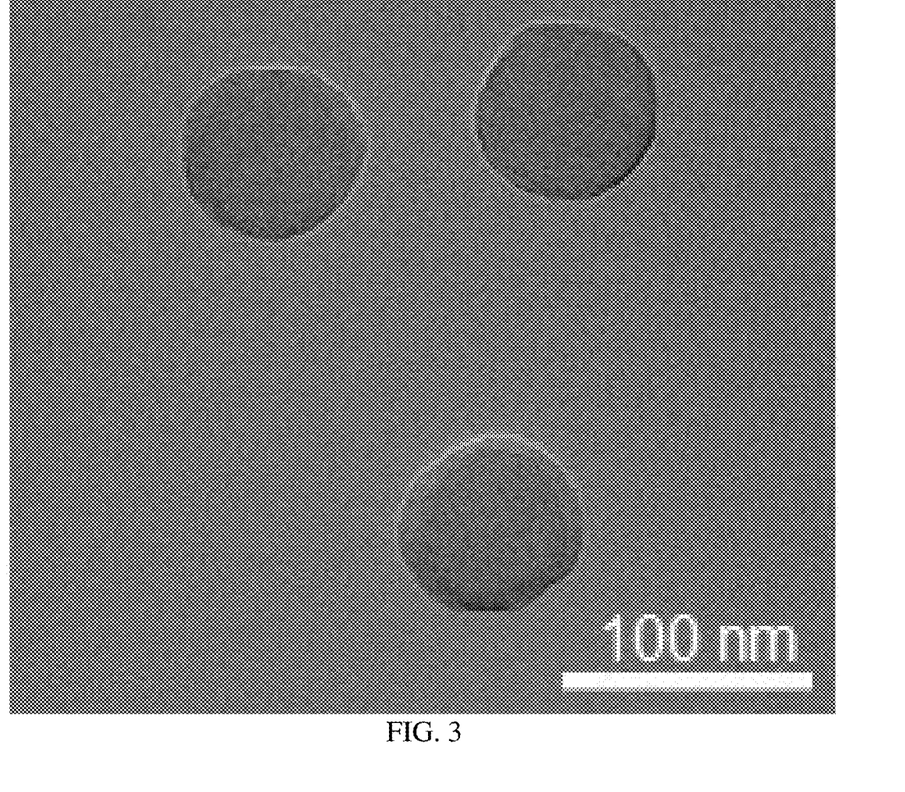
FIG. 3 shows a transmission electron microscope photograph of the iron/shikonin nano-composite as prepared in Example 3, with a size of 70 nm.

Ferric chloride hexahydrate was dissolved in water to obtain a ferric chloride aqueous solution with a concentration of 100 mg/mL; shikonin was dissolved in ethanol to obtain a shikonin ethanol solution with a concentration of 5 mg/mL. 100 µL of the ferric chloride aqueous solution and 5 mL of the shikonin ethanol solution were added in sequence into 41.65 mL of water while stirring at ambient temperature. After stirring at ambient temperature for 1 hour, the resulting mixture was centrifuged at a rotation speed of 15000 rpm for 15 min, for 3 times in total, to obtain an iron/shikonin nano-composite solution, in which the nano-composite has an average size of 70 nm.

Example 4

Figure 4:
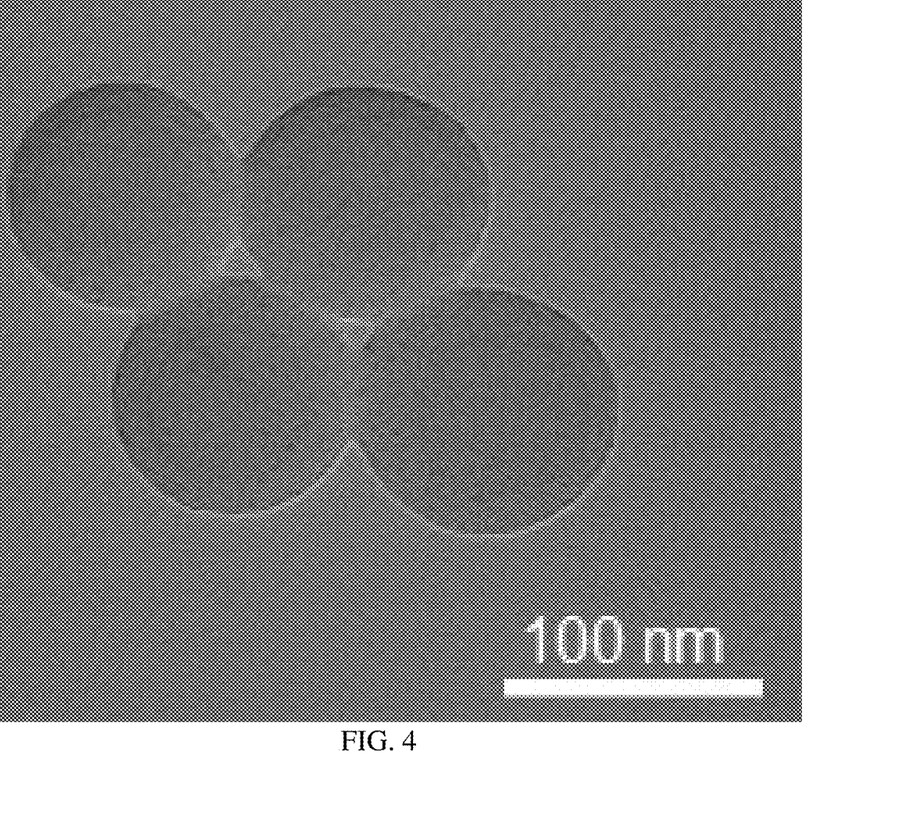
FIG. 4 shows a transmission electron microscope photograph of the iron/shikonin nano-composite as prepared in Example 4, with a size of 90 nm.

Ferric chloride hexahydrate was dissolved in water to obtain a ferric chloride aqueous solution with a concentration of 100 mg/mL; shikonin was dissolved in ethanol to obtain a shikonin ethanol solution with a concentration of 5 mg/mL. 50 µL of the ferric chloride aqueous solution and 5 mL of the shikonin ethanol solution were added in sequence into 41.70 mL of water while stirring at ambient temperature. After stirring at ambient temperature for 1 hour, the resulting mixture was centrifuged at a rotation speed of 15000 rpm for 15 min, for 3 times in total, to obtain an iron/shikonin nano-composite solution, in which the nano-composite has an average size of 90 nm.

It can be seen from Examples 1 to 4 that the size of iron/shikonin nano-composite can be adjusted by changing the amount of ferric salt. The size of the nano-particles decreased with an increase of the amount of ferric salt.

Example 5

Figure 5:
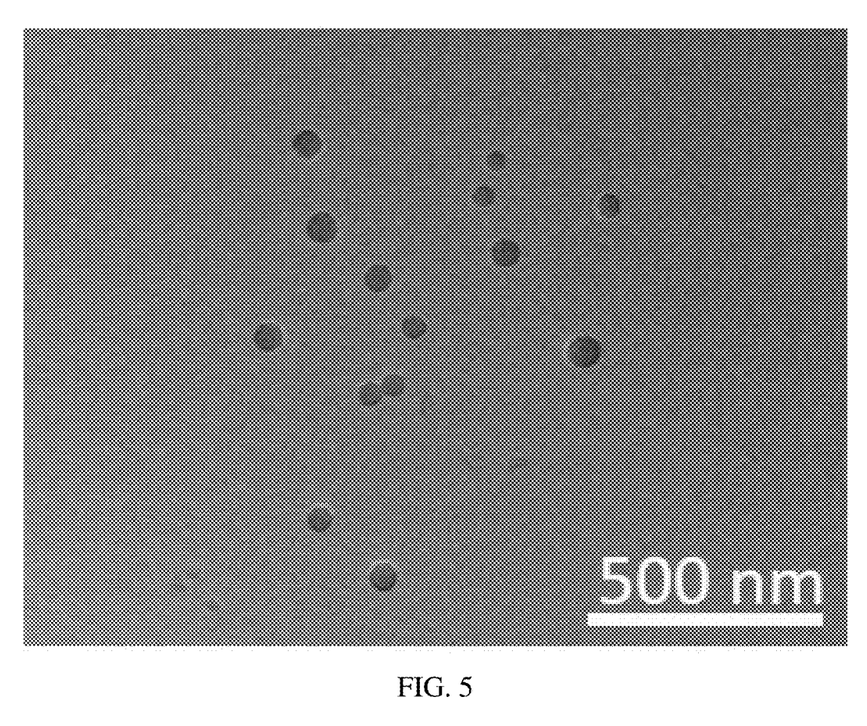
FIG. 5 shows a transmission electron microscope photograph of the iron/shikonin nano-composite as prepared in Example 5, with a size of 60 nm.

Ferric chloride hexahydrate was dissolved in water to obtain a ferric chloride aqueous solution with a concentration of 100 mg/mL; shikonin was dissolved in dimethylformamide to obtain a shikonin dimethylformamide solution with a concentration of 5 mg/mL. 1 mL of the ferric chloride aqueous solution and 5 mL of the shikonin dimethylformamide solution were added in sequence into 40.75 mL of water while stirring at ambient temperature. After stirring at ambient temperature for 1 hour, the resulting mixture was centrifuged at a rotation speed of 15000 rpm for 15 min, 3 times in total, to obtain an iron/shikonin nano-composite solution, in which the nano-composite has an average size of 60 nm.

Example 6

Figure 6:
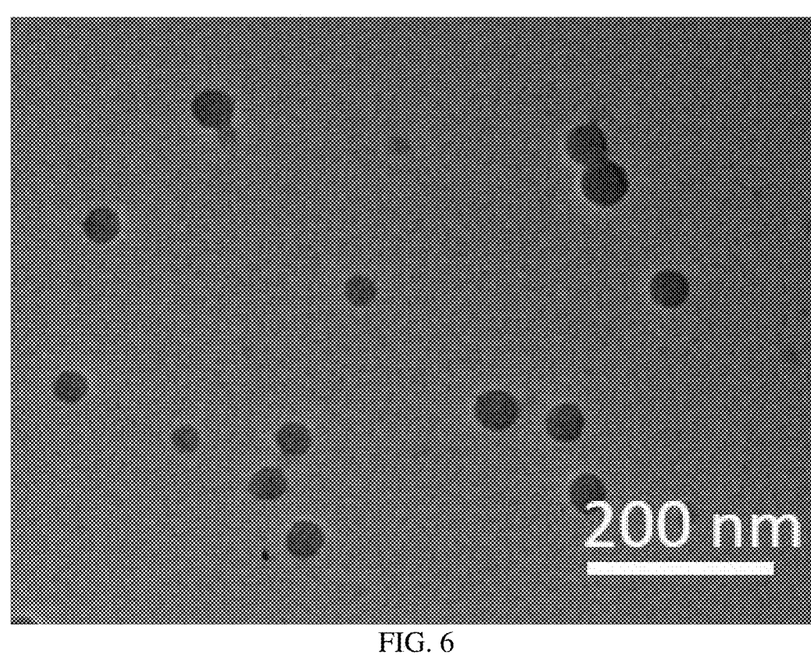
FIG. 6 shows a transmission electron microscope photograph of the iron/shikonin nano-composite as prepared in Example 6, with a size of 50 nm.
Figure 7:
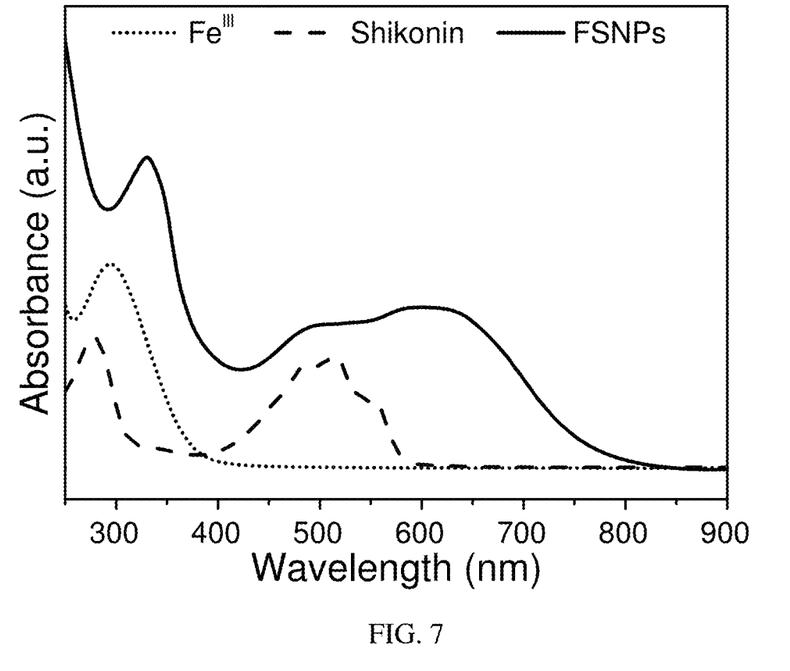
FIG. 7 shows ultraviolet-visible absorption spectra of the iron/Shikonin nano-composite (FSNPs) as prepared in Example 2, shikonin and ferric salt (Fe). It can be seen from the ultraviolet-visible absorption spectra that compared with shikonin, the newly formed iron/shikonin nano-composite (FSNPs) exhibits a new broad dispersion peak at 602 nm, which is attributed to the charge transfer transition caused by the coordination bond between the organic ligand shikonin and the central iron ion, confirming the formation of the iron/shikonin nano-composite.

Ferric nitrate nonahydrate was dissolved in water to obtain a ferric nitrate aqueous solution with a concentration of 400 mg/mL; shikonin was dissolved in ethanol to obtain a shikonin ethanol solution with a concentration of 5 mg/mL. 1 mL of the ferric nitrate aqueous solution and 5 mL of the shikonin ethanol solution were added in sequence into 40.75 mL of water under stirring at ambient temperature. After stirring at ambient temperature for 1 hour, the resulting mixture was centrifuged at a rotation speed of 15000 rpm for 15 min, for 3 times in total, to obtain an iron/shikonin nano-composite solution, in which the nano-composite has an average size of 50 nm.

Example 7

Figure 8A:
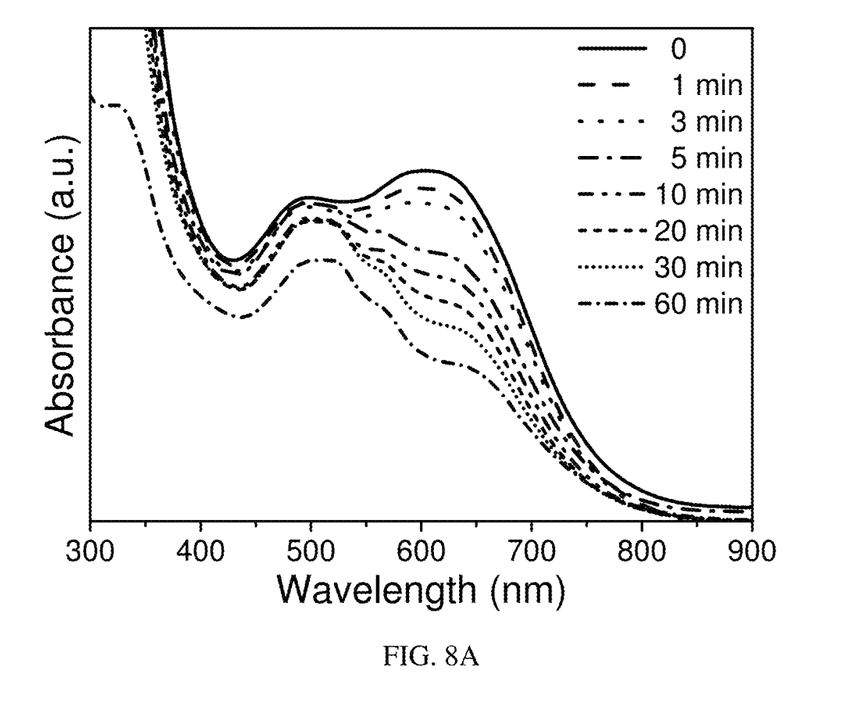
FIG. 8A shows the ultraviolet-visible absorption spectra of nano-composite in a 2 mM glutathione solution at different times.
Figure 8B:
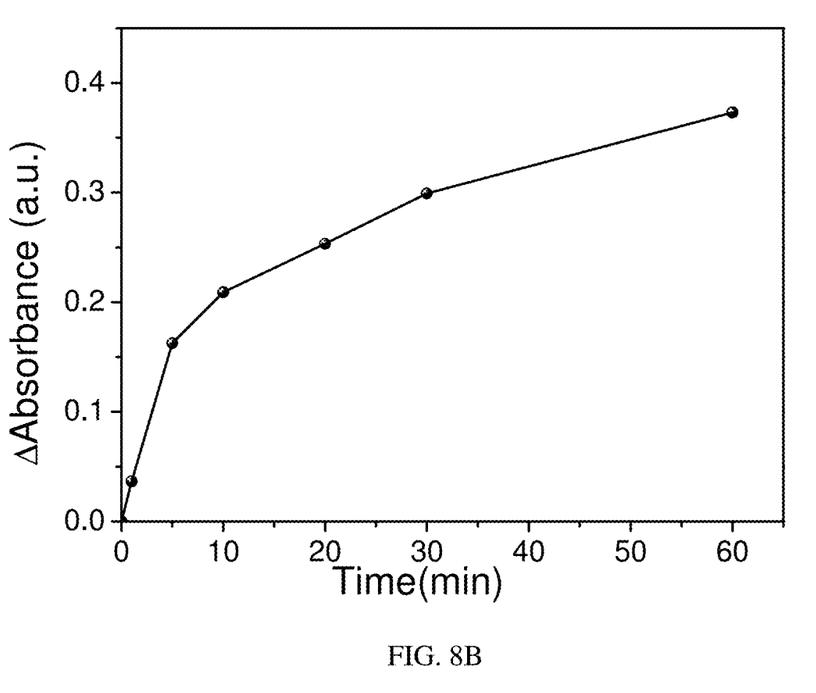
FIG. 8B shows variations of the absorption value of the nano-composite in a glutathione solution with a concentration of 2 mM at 602 nm (peak position of nano-composite). It can be seen from FIG. 8A and FIG. 8B that the absorption value at 602 nm of the iron/shikonin nano-composite decreases gradually, indicating that the intensity of coordination peak gradually weakens and the nano-drugs are disassembled.
Figure 8C:
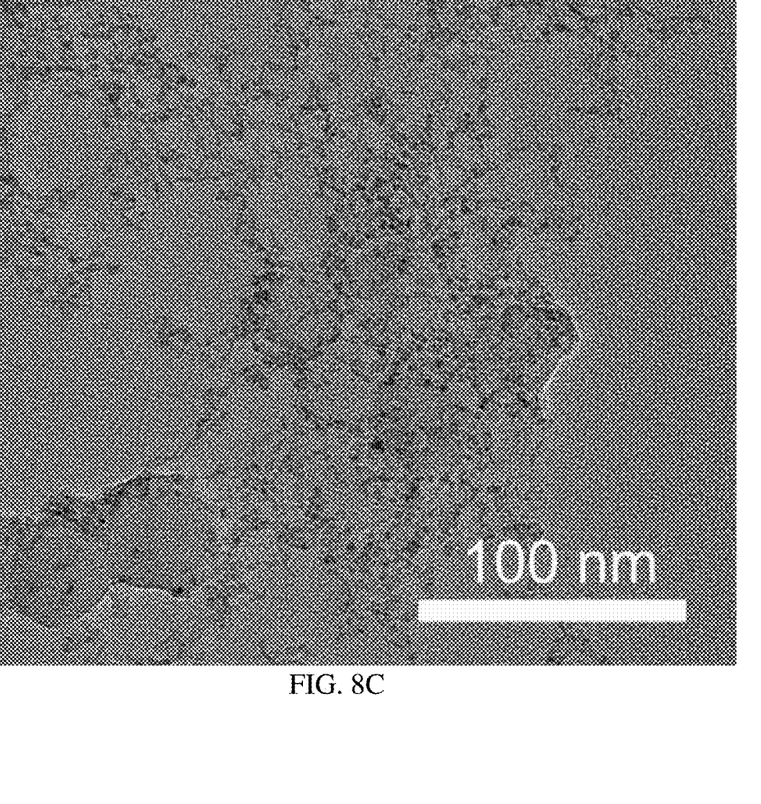
FIG. 8C shows a transmission electron micrograph of the nano-composite after 1 hour in a glutathione solution with a concentration of 2 mM. It can be seen that the structure of the iron/shikonin nano-composite is broken up and the morphology thereof is changed, which further confirms the disassembly of the nano-drugs.

The iron/shikonin nano-composite as prepared by Example 2 was dispersed in a glutathione solution with a concentration of 2 mM, and the ultraviolet-visible absorption spectra of the nano-composite at the initial, 1 min, 3 min, 5 min, 10 min, 20 min, 30 min and 60 min were recorded. After 60 min, a sample was taken for transmission electron microscope photos.

Example 8

Figure 9:
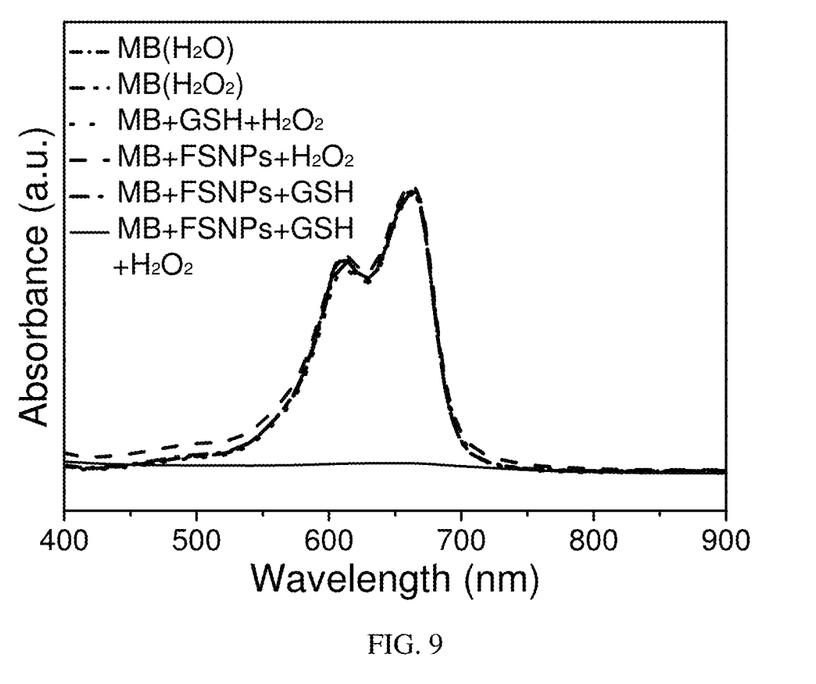
FIG. 9 shows ultraviolet-visible absorption spectra of methylene blue, which shows effects of iron/shikonin nano-composite as prepared in Example 8 on the degradation of methylene blue under different conditions, showing that after redox reaction between ferric iron in the nano-drug and glutathione, the structure of the nano-drug is disassembled, thereby releasing ferrous irons; ferrous irons undergo Fenton reaction and generate hydroxyl radicals, which degrade methylene blue.

MB+FSNPs+GSH+$H_2O_2$ group: an iron/shikonin nano-composite (FSNPs) was dispersed in 2 mL of a glutathione (GSH) solution with a concentration of 2 mM for 1 h, such that the concentration of the iron/shikonin nano-composite is 50 µg/mL, and a centrifugation was performed, obtaining a mixture; 45 µL of a methylene blue (MB) solution with a concentration of 1 mg/mL and 20 µL of a hydrogen peroxide ($H_2O_2$) solution with a concentration of 10 mM were added to the mixture above; after standing for 15 min, the resulting mixture was subjected to an ultraviolet-visible absorption analysis and the spectrum was recorded.

MB+FSNPs+GSH group: an iron/shikonin nano-composite (FSNPs) was dispersed in 2 mL of a glutathione (GSH) solution with a concentration of 2 mM for 1 h, such that the concentration of iron/shikonin nano-composite is 50 µg/mL, and a centrifugation was performed, to obtain a mixture; 45 µL of a methylene blue (MB) solution with a concentration of 1 mg/mL was added to the mixture above; after standing for 15 min, the resulting mixture was subjected to an ultraviolet-visible absorption analysis and the spectrum was recorded.

MB+FSNPs+$H_2O_2$ group: 45 µL of a methylene blue (MB) solution with a concentration of 1 mg/mL and 20 µL of a hydrogen peroxide ($H_2O_2$) solution with a concentration of 10 mM were added to 2 mL of an iron/shikonin nano-composite (FSNPs) aqueous solution (the concentration of the iron/shikonin nano-composite is 50 µg/mL); after standing for 15 min, the resulting mixture was subjected to an ultraviolet-visible absorption analysis and the spectrum was recorded.

MB+GSH+$H_2O_2$ group: 45 µL of a methylene blue (MB) solution with a concentration of 1 mg/mL and 20 µL of a hydrogen peroxide ($H_2O_2$) solution with a concentration of 10 mM were added to 2 mL of a glutathione solution with a concentration of 2 mM; after standing for 15 min, the resulting mixture was subjected to an ultraviolet-visible absorption analysis and the spectrum was recorded.

MB+$H_2O_2$ group: 45 µL of a methylene blue (MB) solution with a concentration of 1 mg/mL and 20 µL of a hydrogen peroxide ($H_2O_2$) solution with a concentration of 10 mM were added to 2 mL of water; after standing for 15 min, the resulting mixture was subjected to an ultraviolet-visible analysis and the spectrum was recorded.

MB+$H_2O$ group: 45 µL of a methylene blue (MB) solution with a concentration of 1 mg/mL was added to 2 mL of water; after standing for 15 min, the resulting mixture was subjected to an ultraviolet-visible analysis and the spectrum was recorded.

It can be seen from Example 8 that compared with other groups, in the MB+FSNPs+GSH+$H_2O_2$ group, the methylene blue solution became colorless from blue, and the absorption peaks of the ultraviolet-visible absorption spectrum disappeared, indicating that after being disassembled in the glutathione solution, the iron/shikonin nano-composite could release ferrous ions, which underwent Fenton reaction with hydrogen peroxide and generated hydroxyl radicals, which degraded methylene blue.

Example 9

Figure 10:
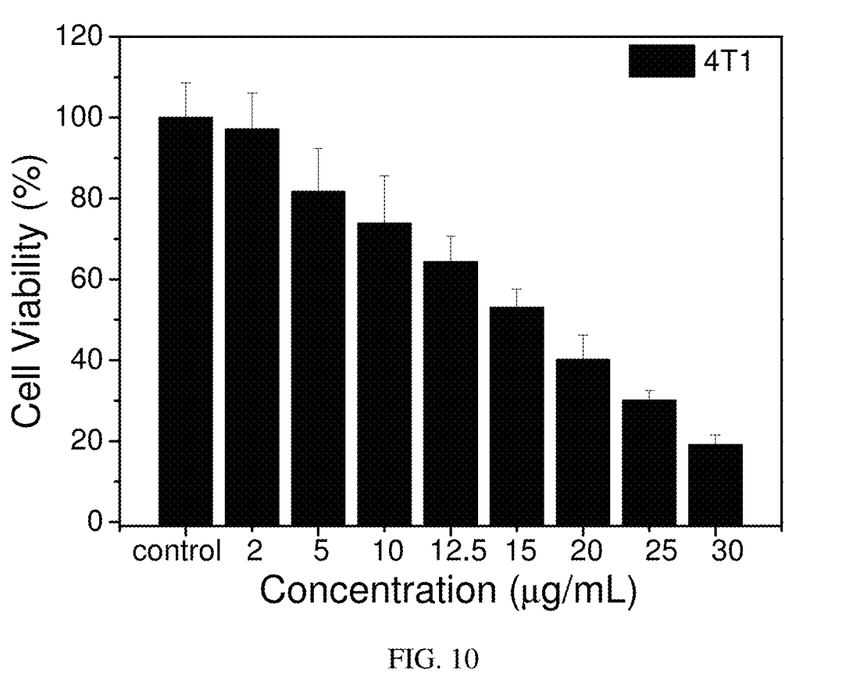
FIG. 10 shows a cck8 cytotoxicity test chart of the iron/shikonin nano-composite as prepared in Example 9. It can be seen from this chart that the cell survival rate of cancer cells is dependent on the concentration of nano-drug, wherein the cell survival rate of cancer cells gradually decreases with an increase of the concentration of nano-drug, indicating that the nano-drug has a great ability of killing cancer cells.

4T1 cells (purchased from Beyotime Biotechnology Co., Ltd.) were inoculated in a 96-well culture plate with an initial density of $1\times10^4$ cells per well and incubated for 24 hours; then the cells were co-cultured with iron/shikonin nano-composite solutions with concentrations of 2 μg/mL, 5 μg/mL, 10 μg/mL, 12.5 μg/mL, 15 μg/mL, 20 μg/mL, 25 μg/mL and 30 μg/mL respectively for 24 hours; then, 10 μL of cck8 (Cell Counting Kit-8, purchased from bimake.cn) was added to each well, and the survival rate of cells in each well was tested with a microplate reader one hour later.

The results of Example 9 showed that the survival rate of breast cancer cells in 4T1 mice gradually decreased with the increase of the concentration of the iron/shikonin nano-composite, and when the concentration reached 30 μg/mL, the survival rate of cells was only 20%, indicating that the nano-composite had a great ability of killing cancer cells.

What is claimed is:

1. A method for preparing an iron/shikonin nano-composite, comprising,
   adding an aqueous solution of a ferric salt into water while stirring at ambient temperature;
   adding an organic solvent solution of shikonin, wherein the organic solvent is miscible with water;
   continuously stirring at ambient temperature;
   centrifuging the resulting mixture to purify, thereby obtaining an iron/shikonin nano-composite solution; and
   evaporating the iron/shikonin nano-composite solution to dryness to obtain an iron/shikonin nano-composite solid powder.

2. The method of claim 1, wherein the organic solvent is selected from the group consisting of: methanol, ethanol, isopropanol, acetonitrile, glycerol, acetone, dimethyl sulfoxide, tetrahydrofuran, and dimethylformamide.

3. The method of claim 1, wherein the ferric salt is selected from the group consisting of: ferric chloride, ferric nitrate, and ferric sulfate.

4. The method of claim 1, wherein a molar ratio of the ferric salt to shikonin is in a range of (0.1-12): 1; a concentration of shikonin in the organic solvent solution of shikonin is in a range of 1-10 mg/mL; and a concentration of the ferric salt in the aqueous solution of the ferric salt is in a range of 50-800 mg/mL.

5. The method of claim 1, wherein continuous stirring at ambient temperature comprises maintaining stirring for 30 min to 24 h.

6. An iron/shikonin nano-composite, which is prepared by the method of claim 1.

7. The iron/shikonin nano-composite of claim 6, wherein the iron/shikonin nano-composite has a diameter of 10-200 nm.

8. A method for treating cancer, comprising administering the iron/shikonin nano-composite of claim 6 to a subject in need thereof.

9. An iron/shikonin nano-composite, which is prepared by adding an aqueous solution of a ferric salt into water while stirring at ambient temperature;
   adding an organic solvent solution of shikonin, wherein the organic solvent is miscible with water;
   continuously stirring at ambient temperature; and
   centrifuging the resulting mixture to purify, thereby obtaining an iron/shikonin nano-composite in a resulting solution.

10. A method for treating cancer, comprising administrating the iron/shikonin nano-composite of claim 9 to a subject in need thereof.

11. The iron/shikonin nano-composite of claim 6, wherein the iron/shikonin nano-composite has a diameter of 30-90 nm.

12. The iron/shikonin nano-composite of claim 6, wherein the iron/shikonin nano-composite has a diameter of 50-70 nm.

13. The iron/shikonin nano-composite of claim 6, wherein the iron/shikonin nano-composite has a diameter of 60 nm.

14. The method of claim 4, wherein the molar ratio of the ferric salt to shikonin is 11.5:1, 4.3:1, 2.1:1, 0.4:1, or 0.2:1.

* * * * *